(12) United States Patent
Al-Enezi

(10) Patent No.: US 9,702,837 B2
(45) Date of Patent: Jul. 11, 2017

(54) SYSTEM FOR MEASURING GLASS TRANSITION TEMPERATURE OF A POLYMER

(71) Applicant: KUWAIT INSTITUTE FOR SCIENTIFIC RESEARCH, Safat (KW)

(72) Inventor: Salah T. Al-Enezi, Kuwait (KW)

(73) Assignee: KUWAIT INSTITUTE FOR SCIENTIFIC RESEARCH, Safat (KW)

( * ) Notice: Subject to any disclaimer, the term of this patent is extended or adjusted under 35 U.S.C. 154(b) by 485 days.

(21) Appl. No.: 14/558,646

(22) Filed: Dec. 2, 2014

(65) Prior Publication Data

US 2016/0153921 A1   Jun. 2, 2016

(51) Int. Cl.
| | |
|---|---|
| G01N 25/12 | (2006.01) |
| G01N 33/44 | (2006.01) |
| G01N 25/00 | (2006.01) |
| G01N 25/02 | (2006.01) |
| G01N 25/04 | (2006.01) |
| G01N 33/38 | (2006.01) |

(52) U.S. Cl.
CPC .......... *G01N 25/04* (2013.01); *G01N 33/386* (2013.01); *G01N 33/44* (2013.01)

(58) Field of Classification Search
CPC .......... G01N 25/04; G01N 25/12; G01N 3/20; G01N 33/386; G01K 17/00; G01K 17/04
USPC ............................................ 422/51; 436/147
See application file for complete search history.

(56) References Cited

U.S. PATENT DOCUMENTS

| | | | |
|---|---|---|---|
| 5,248,199 A * | 9/1993 | Reading | G01N 25/4833 374/11 |
| 5,955,511 A | 9/1999 | Handa et al. | |
| 6,447,859 B2 | 9/2002 | Oguro et al. | |
| 6,491,425 B1 * | 12/2002 | Hammiche | B82Y 35/00 374/10 |
| 6,534,005 B1 * | 3/2003 | Strahm | G01N 25/12 422/51 |

(Continued)

FOREIGN PATENT DOCUMENTS

JP       2004-325426       11/2004

OTHER PUBLICATIONS

"Measurement of Tg," University of Cambridge website.

(Continued)

*Primary Examiner* — Gail Kaplan Verbitsky
(74) *Attorney, Agent, or Firm* — Richard C. Litman

(57) ABSTRACT

A system for measuring glass transition temperature of a polymer can include a cell having a closed bottom and a peripheral wall extending from the bottom, a sample holder having a first supporting pin and a second supporting pin spaced apart from the first supporting pin, a loading probe in the cell for selectively contacting a polymer sample disposed on the sample holder, a temperature probe in the cell, a heater in the cell, a temperature sensor, a source of pressure, a source of gas in communication with the cell, and a data acquisition system operably connected to the loading probe, the temperature probe and the source of pressure. The first and second supporting pins and the loading probe in the cell provide a three-point flexural bending assembly for measuring bending of the polymer sample under varied conditions of temperature and pressure in the presence of a gas.

13 Claims, 4 Drawing Sheets

(56) References Cited

U.S. PATENT DOCUMENTS

| | | | | |
|---|---|---|---|---|
| 6,543,931 | B2* | 4/2003 | Sauvant | G01N 25/12 324/663 |
| 6,716,638 | B1* | 4/2004 | Hsiung | G01N 25/72 136/201 |
| 7,078,164 | B1* | 7/2006 | Diamond | C08F 110/14 422/514 |
| 7,448,798 | B1* | 11/2008 | Wang | G01Q 60/58 374/163 |
| 8,231,267 | B2* | 7/2012 | Schick | G01N 25/4866 374/10 |
| 8,484,759 | B2* | 7/2013 | Jesse | B82Y 35/00 374/100 |
| 8,858,070 | B2* | 10/2014 | Zaldivar | G01N 25/04 374/16 |
| 2002/0048306 | A1* | 4/2002 | Sauvant | G01N 25/12 374/21 |
| 2007/0155905 | A1 | 7/2007 | Drewniak et al. | |
| 2007/0212548 | A1 | 9/2007 | Lefaux et al. | |
| 2011/0068262 | A1* | 3/2011 | Vorst | G01B 21/08 250/282 |
| 2012/0140790 | A1* | 6/2012 | Ali | A61K 9/0019 374/31 |
| 2012/0296040 | A1 | 11/2012 | Kodama | |
| 2012/0307860 | A1* | 12/2012 | Zaldivar | G01N 25/04 374/16 |
| 2013/0100981 | A1* | 4/2013 | Lee | G01N 25/02 374/17 |
| 2014/0010259 | A1* | 1/2014 | Stevick | F16K 17/16 374/46 |

OTHER PUBLICATIONS

Boyer et al., Modification of the glass transitions of polymers by high-pressure gas solubility, Pure Appl. Chem., 2005, vol. 77, No. 3, pp. 593-603.

* cited by examiner

SYSTEM FOR MEASURING GLASS TRANSITION TEMPERATURE OF A POLYMER

BACKGROUND OF THE INVENTION

1. Field of the Invention

The present invention relates to systems for measuring properties of polymers, and particularly, to a system for measuring glass transition temperature ($T_g$) of polymers blanketed with a gas phase at high pressures.

2. Description of the Related Art

Glass transition temperature ($T_g$) of a polymeric material can significantly affect the mechanical properties of the polymeric material. The glass transition temperature is the temperature at which the polymer transitions from a hard, glass-like state to a rubber-like state. The glass transition state is associated with cooperative motion among a large number of chain segments, including those from neighboring polymer chains.

Typically, the glass transition temperature, (Tg), is determined using the following techniques: Differential Scanning calorimetry (DSC); Thermo-Mechanical Analysis (TMA); and Dynamic Mechanical Analysis (DMA). DSC defines the glass transition as a change in the heat capacity as the polymer matrix goes from a glassy state to a rubbery state. This is a second order endothermic transition, requiring heat to go through the transition. Thus, in the DSC measurement, the transition appears as a step transition rather than as a peak transition, such as might be seen with a melting transition. TMA defines the glass transition in terms of the change in the coefficient of thermal expansion (CTE) as the polymer goes from glass to rubber state with the associated change in the free molecular volume. DMA measures the viscoelastic moduli, storage and loss modulus, damping properties, and tan delta of materials as they are deformed under a period (sinusoidal) deformation (stress or strain). The DSC measures a heat flow effect, whereas the TMA is measuring a physical effect, i.e., the expansion in the two directions. Both techniques assume that the effect happens over a narrow range of a few degrees in temperature. However, if the glass transition is very broad it may not be seen with either approach.

In order to make a polymer more flexible and easier to handle, a plasticizer is generally added to the polymer (usually amorphous), which lowers its glass transition temperature. The plasticization effect on polymers is used widely as a processing aid. Due to its ability to plasticize, $CO_2$ at high pressure is widely used for extraction, impregnation, polymerization, foaming and shape forming of polymers.

The assessment of $T_g$ of a polymeric material at high pressure assumes prime importance when a plasticizer, such as $CO_2$, is intended to be used to facilitate processing. In this regard, a real-time technique to monitor the effect of plasticization in-situ and to measure the glass transition behavior of a two phase polymer/gas system at high pressures in the gaseous atmosphere would be useful.

Thus, a system for measuring glass transition temperature (Tg) behavior of polymers at high pressure solving the aforementioned problems is desired.

SUMMARY OF THE INVENTION

A system for measuring glass transition temperature of a polymer can include a cell having a closed bottom and a peripheral wall extending from the bottom, a sample holder in the cell having a first supporting pin and a second supporting pin spaced apart from the first supporting pin, a loading probe adjustable at least between a raised position and a lowered position for selectively contacting a polymer sample disposed on the sample holder, a temperature probe for measuring a temperature of the polymer sample, a heater, a temperature sensor for measuring a temperature within the cell, a source of pressure in communication with the cell, a source of gas in communication with the cell, and a data acquisition system operably connected to the loading probe, the temperature probe and the source of pressure. The first and second supporting pins and the loading probe in the cell provide a three-point flexural bending assembly for measuring bending of the polymer sample under varied conditions of temperature and pressure in the presence of a gas such as $CO_2$.

These and other features of the present invention will become readily apparent upon further review of the following specification and drawings.

DETAILED DESCRIPTION OF THE PREFERRED EMBODIMENTS

Figure 1:
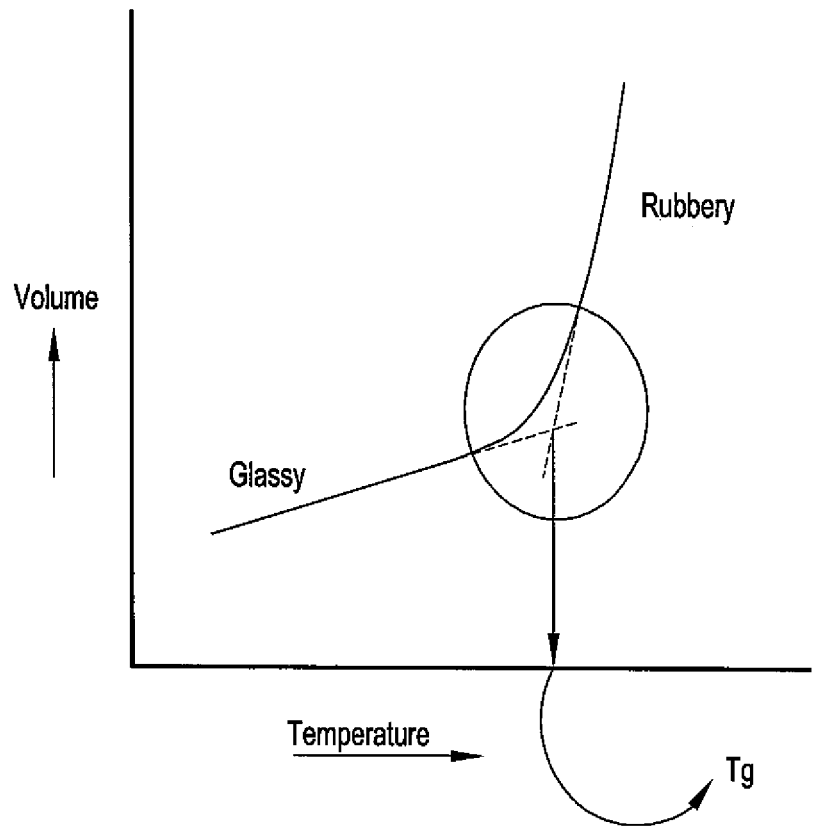
FIG. 1 shows a plot of the polymeric glass transition temperature as a function of volume and temperature.

A system for measuring glass transition temperature ($T_g$) of a polymer can be used to determine the glass transition temperature of a polymer or polymeric materials exposed to a gaseous environment at ambient and high pressures as well as a broad range of temperatures. Thus, the glass transition temperature of polymeric materials as a function of pressure and temperature in a gaseous environment can be measured using the present system. As used herein and illustrated in FIG. 1, the glass transition temperature is the temperature at which a polymeric material transforms from a glassy state to a rubbery state.

Figure 2:
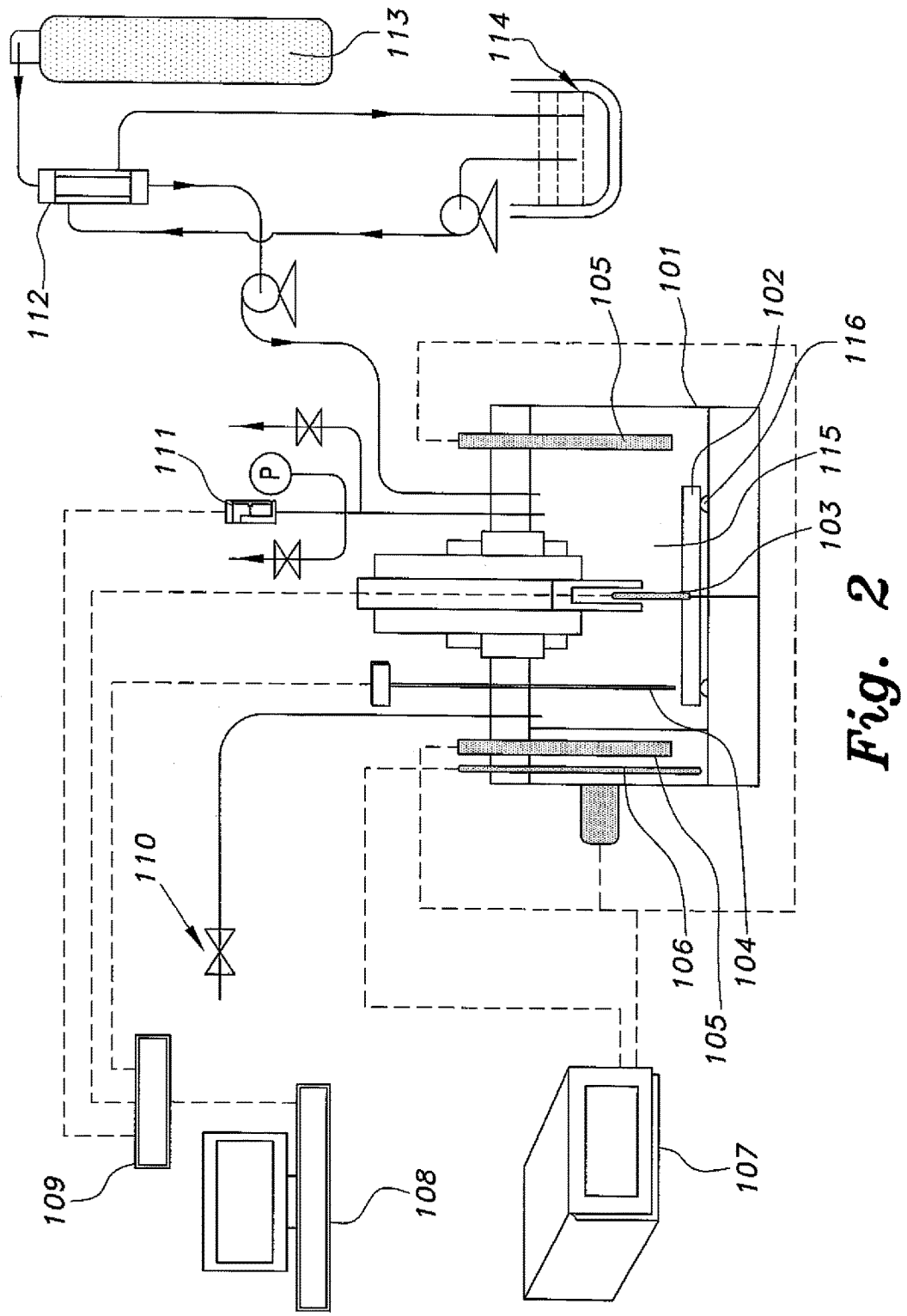
FIG. 2 is a schematic view of the high pressure cell and the set-up to measure $T_g$.

Referring to FIG. 2, the system for measuring glass transition temperature of a polymer 100 can include a cell 101, a sample holder 116 disposed in the cell for retaining a sample polymeric sample 102, a loading probe 103 that extends into the cell 101 from a top portion of the cell 101 toward a center portion of the polymeric sample 102, a temperature probe 104 that extends into the cell from the top portion and is configured to periodically contact the polymeric sample 102 for measuring the temperature of the polymeric sample 102, a heater 105 for heating the cell 101, a temperature sensor 106, e.g., a temperature sensor thermocouple, for measuring the temperature of the cell 101 coupled to a temperature controller 107, a source of pressure (pressure transducer) 111, a source of gas 113, e.g., $CO_2$ gas for providing a gaseous environment 115 in the cell 101, and a data acquisition system 109 coupled to a computer 108. The data acquisition system can be operably connected to the loading probe 103, the temperature probe 104, and the source of pressure 111 for logging information acquired therefrom. The data acquisition system can be a self-contained high accuracy data logger for use with PCs. A logger such as PICO-ACC 16 (Alison Technology Corporation, Kingsville, Tex.) can be used, for example. A back pressure regulator 110 can also be provided to regulate back pressure leaving the cell 101. The source of gas 113 can be operably connected to a heat exchanger 112 and an ice bath 114.

Figure 3A:
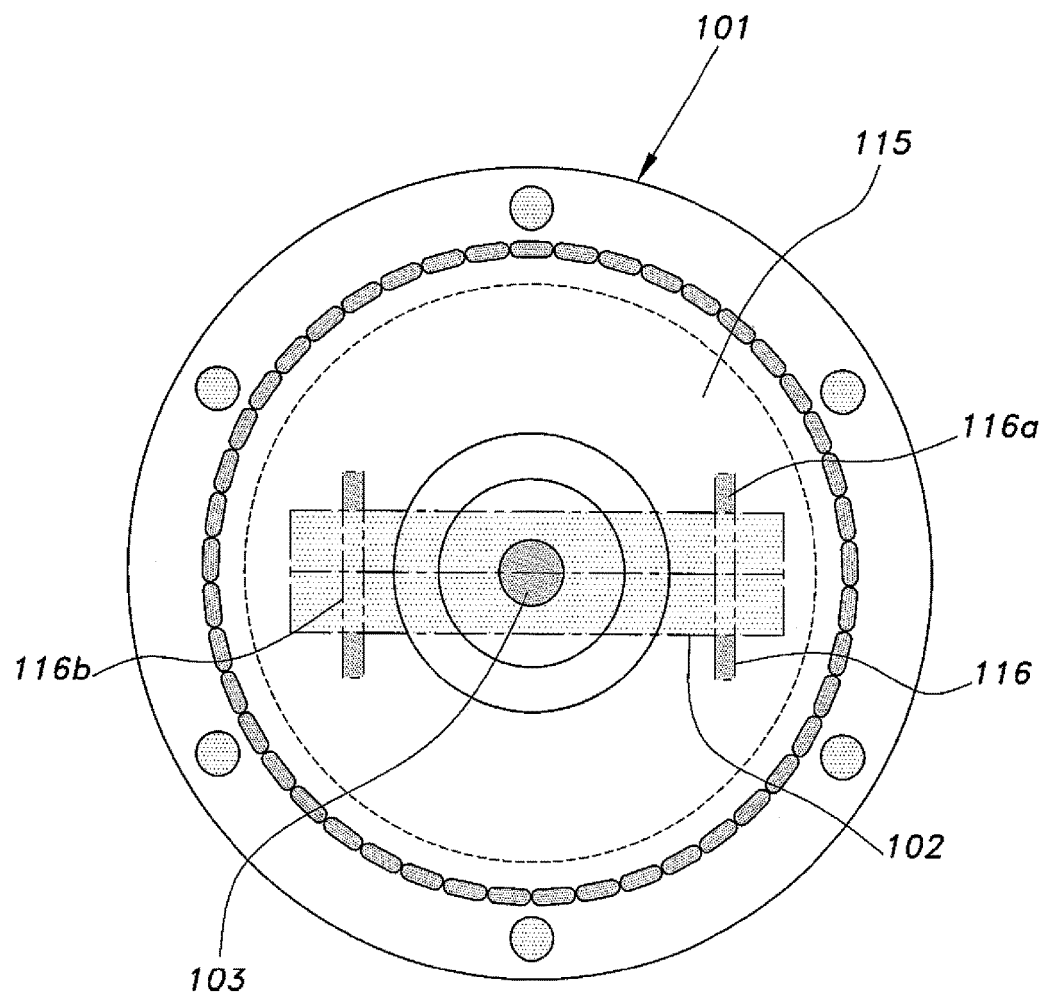
FIG. 3A depicts the top view of the high pressure cell.
Figure 3B:
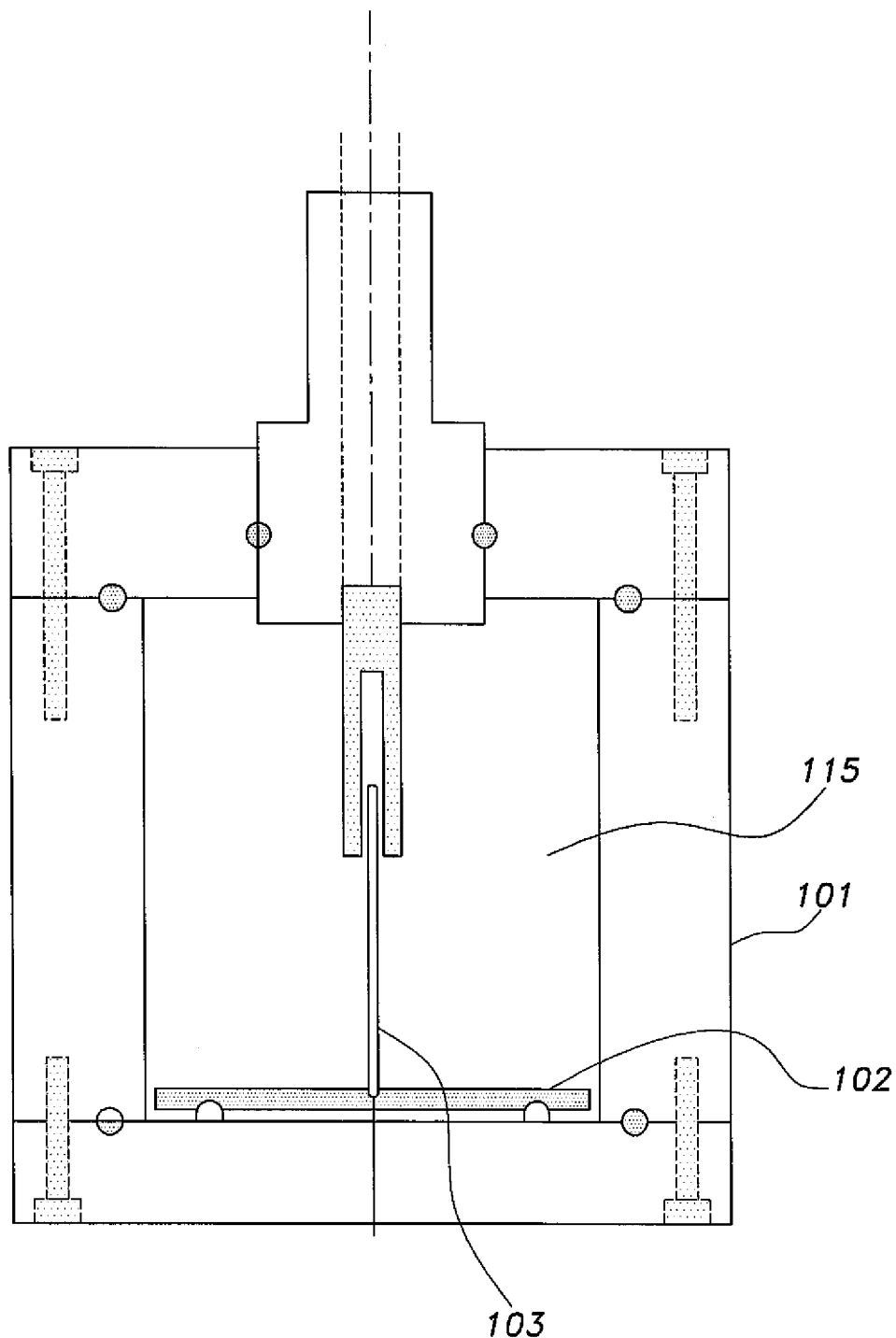
FIG. 3B depicts the side view of the high pressure cell.

FIG. 3A shows a top view of the cell 101. As can be seen, the sample holder 116 can include a first supporting pin 116a and a second supporting pin 116b that is spaced apart from the first supporting pin 116a. Opposing ends or end portions of the sample 102 may be disposed on supporting pins 116a and 116b, respectively. FIG. 3B shows a side view of the cell 101, with the loading probe 103 contacting the sample 102. The loading probe 103 is disposed above a center portion of the sample 102 or above a point approximately midway between the first supporting pin 116a and the second supporting pin 116b. The loading probe 103 can contact the sample 102 that is placed on the sample holder 116. For example, the loading probe 103 can be adjustable between at least a raised position and a lowered position for selectively bearing upon a surface of the polymer sample 102. The loading probe 103 can be a linear variable displacement transducer (LVDT) probe. The loading probe 103 and the supporting pins 116a and 116b can together provide a three-point bending flexural assembly for measuring bending of the polymer sample 102, which is described in further detail herein.

The cell 101 can withstand temperatures up to about 300° C. and pressures up to about 200 bar. The cell 101 can be made from any suitable material. Preferably, the cell 101 is made from steel and is cylindrical in shape. The glass transition measurement is taken when the sample begins to change phase from a glassy to a rubbery phase.

In the cell 101, the polymer sample 102 can be exposed to a gaseous environment, for example a $CO_2$ environment at a high pressure. For example, the temperature can be raised to temperatures as high as 300° C. The pressure can be raised from ambient pressure to pressures as high as 200 bar. Sorption of the $CO_2$ gas, as well as increased pressure and temperature conditions within the cell can cause softening of the polymer sample 102. The extent of softening (which depends on the $T_g$ at that thermodynamic condition) under the conditions of increased temperature and pressure can be measured using the three-point-flexural bending assembly, as described above. The three-point flexural bending assembly can measure bending of the polymer sample 102. Once the polymer sample 102 is placed on supporting pins 116a and 116b, the loading probe 103 can be lowered at a constant rate onto a portion, e.g., central portion, of the polymer sample 102 until the polymer sample 102 bends. An onset temperature or temperature at which deflection occurs (polymer sample 102 is displaced as a result of the pressure exerted by the loading probe 103) can be recorded. For example, the temperature at which deflection, e.g., central deflection, suddenly begins to increase, can be recorded as the nominal gas transition temperature for the polymer sample 102. A central deflection of about 5 mm is typically indicative of a phase change, at which point the nominal gas transition temperature can be recorded. The $T_g$ measurement can be performed under both isothermal and non-isothermal conditions. The polymer sample 102 can have any suitable thickness. For example, the polymer sample 102 can be about 2-3 mm in thickness.

Carbon dioxide ($CO_2$) gas can, at high pressure, lower the glass transition temperature of polymers because of the effect and ability of $CO_2$ to act as a plasticizer. The three-point flexural bending mode measurement, as described herein, can measure the extent of softening of a polymer sample as a function of temperature/pressure. The glass transition temperature values of polymers tested using the present system were in agreement with those reported in the literature and those obtained using other techniques. For example, the onset temperature at which the central deflection suddenly began to increase (about 5 mm) correlates well with the glass transition temperature value reported in the literature. The experimental $T_g$ values obtained were validated by comparing with $T_g$ values obtained using other conventional techniques, like differential scanning calorimetry (DSC), and found to be within ±2%. Thus, the bending onset temperature determined by the present system is the glass transition temperature of a polymer at the specified atmospheric pressure conditions provided in the cell.

The plasticization effect of gases in the supercritical state can be better controlled based on the $T_g$ values obtained by the present system. Further, unlike alternate conventional methods like DSC, which have significant pressure limitations (maximum allowable pressure is approximately 69 bar), the present system can determine the $T_g$ value of a polymer/gas phase system up to pressures of about 200 bar at temperatures up to about 300° C. Thus, the present system is capable of determining the glass transition temperature of polymeric materials exposed to a gaseous environment at ambient and high pressures, over a broad range of temperatures. Also, since there is no dependence on the viscoelastic properties of the polymer, the $T_g$ values are more universal. Further, the pressure dependence of the glass transition temperature, which is one of the key issues regarding the validity of existing free volume theories, can be studied easily and accurately with the present system. Finally, the present system allows for predicting the glass transition behavior of polymers that maybe subjected to contact with gases.

The sorption of fluids, including gases in the supercritical state induces significant plasticization, which results in a substantial decrease of the glass-transition temperature. In view of the extensive use of supercritical carbon dioxide to swell and plasticize polymers in various processes, the present system can be used to simulate the intended end-use environment of the polymer and monitor the effect of plasticization in-situ (real-time). The present system allows measurement of the glass transition temperature of a polymer when the polymer is blanketed in the gas phase at high pressure, rather than measuring the glass transition temperature of the polymer in isolation. As such, the present system enables researchers to predict the glass transition behavior of polymers which may be subjected to contact with gases.

It is to be understood that the present invention is not limited to the embodiments described above, but encompasses any and all embodiments within the scope of the following claims.

I claim:
1. A system for measuring glass transition temperature of a polymer, comprising:
   a cell having a closed bottom and a peripheral wall extending from the bottom;
   a sample holder disposed on the cell bottom for retaining a polymer sample thereon, the sample holder including a first supporting pin and a second supporting pin, the second supporting pin being spaced apart from the first supporting pin;
   a loading probe adjustable between at least a raised and a lowered position for selectively contacting the polymer sample;
   a temperature probe extending into the cell for measuring a temperature of the polymer sample;
   a heater in communication with the cell for heating the cell;

a temperature sensor in communication with the cell for measuring a temperature within the cell;

a source of pressure in communication with the cell;

a source of gas in communication with the cell; and a data acquisition system operably connected to the loading probe, the temperature probe and the source of pressure;

whereby the first and second supporting pins and the loading probe provide a three-point flexural bending assembly for measuring bending of the polymer sample under varied conditions of temperature and pressure.

2. The system of claim 1, wherein the cell is a steel cell.

3. The system of claim 1, wherein the source of gas is a source of $CO_2$ gas.

4. The system of claim 1, wherein the cell can withstand temperatures as high as 300° C. and pressures as high as 200 bar.

5. The system of claim 1, wherein the loading probe is a linear variable displacement transducer (LVDT) probe.

6. The system of claim 1, wherein the temperature probe is a platinum resistance thermometer (PRT).

7. The system of claim 1, wherein the data acquisition system is operably connected to a computer.

8. The system of claim 1, wherein the source of pressure comprises a pressure transducer.

9. The system of claim 1, wherein the, the loading probe is suspended above the sample holder between the first supporting pin and the second supporting pin.

10. A method for measuring gas transition temperature of a polymer, comprising providing a system including:

a cell having a closed bottom and a peripheral wall extending from the bottom;

a sample holder disposed on the cell bottom for retaining a polymer sample thereon, the sample holder including a first supporting pin and a second supporting pin, the second supporting pin being spaced apart from the first supporting pin;

a loading probe adjustable between a raised and a lowered position for selectively contacting the polymer sample, the loading probe suspended above the sample holder between the first supporting pin and the second supporting pin;

a temperature probe extending into the cell for measuring a temperature of the polymer sample;

a heater for heating the cell;

a temperature sensor for measuring a temperature within the cell;

a source of pressure in communication with the cell;

a source of gas in communication with the cell; and a data acquisition system operably connected to the loading probe, the temperature probe and the source of pressure;

positioning the polymer sample on the sample holder, such that opposing ends of the polymer sample are approximately aligned with the first supporting pin and the second supporting pin, respectively;

introducing gas into the cell from the source of gas;

increasing the temperature within the cell;

increasing the pressure within the cell;

lowering the loading probe onto the polymer sample until the polymer sample bends or deflects;

recording a temperature of the polymer sample at which deflection suddenly increases as the nominal gas transition temperature for the polymer sample.

11. The method of claim 10 wherein the polymer sample has a thickness of about 2-3 mm.

12. The method of claim 10, wherein the gas is $CO_2$ gas.

13. The method of claim 10, wherein the nominal gas transition temperature is recorded when deflection is about 5 mm.

* * * * *